(12) United States Patent
Hähnlein et al.

(10) Patent No.: US 6,921,754 B2
(45) Date of Patent: Jul. 26, 2005

(54) COMPOSITIONS CONTAINING FOLIC ACID AND REDUCED FOLATE

(75) Inventors: Wolfgang Hähnlein, Freinsheim (DE); Klaus Krämer, Landau (DE); Oliver Hasselwander, Landau (DE); Loni Schweikert, Altrip (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/275,566

(22) PCT Filed: May 3, 2001

(86) PCT No.: PCT/EP01/04984

§ 371 (c)(1),
(2), (4) Date: Nov. 7, 2002

(87) PCT Pub. No.: WO01/84962

PCT Pub. Date: Nov. 1, 2001

(65) Prior Publication Data

US 2003/0143304 A1 Jul. 31, 2003

(30) Foreign Application Priority Data

May 10, 2000 (DE) .......................... 100 22 510

(51) Int. Cl.$^7$ ........................ A61K 31/44; A61K 31/50; A61K 31/70
(52) U.S. Cl. ........................... 514/46; 514/52; 514/249; 514/345
(58) Field of Search ........................ 514/52, 345, 249, 514/46

(56) References Cited

U.S. PATENT DOCUMENTS

| | | |
|---|---|---|
| 4,753,926 A | 6/1988 | Lucas et al. |
| 5,624,686 A | 4/1997 | Shimoda et al. |
| 5,654,011 A * | 8/1997 | Jackson et al. ............. 424/635 |
| 5,997,915 A * | 12/1999 | Bailey et al. ................. 426/72 |

FOREIGN PATENT DOCUMENTS

| | | |
|---|---|---|
| EP | 646 322 | 4/1995 |
| WO | 93/10118 | 5/1993 |
| WO | 97/27764 | 8/1997 |
| WO | 98/19690 | 5/1998 |
| WO | 99/37155 | 7/1999 |

OTHER PUBLICATIONS

The Merck Manual of Diagnosis and Therapy, 14$^{th}$ed., published 1982 by Merck & Co., Inc. (NJ) pp 410–413, 428–435 and 532–535.*
Thermal Stability of Folic Acid . . . , Day et al., Jrl. Food Sci., vol. 48 (1983) 580–599.
Health and Nutritional Benefits of Citrus Fruit Components, Rouseff et al., Nov. 1994, Food Tech. 125–132.
Hages et al, (1966),Geburtsh.Frauenheilk, 56, M59–M65.
Habibzadeh et al. (1986) Br. J. Nutr. vol. 55, p. 23.
Friendship et al., (1991), In. Can. Vet. J., vol. 32, p. 564.
Hankey et al., Lancet, 354, 407–413, no publication date available.
Referenzwerte fur diet Nahrstoffzufuhr. 1. Aufl. Umschau Braus Verlag, Frankfurt, herausgegeben von der Deutschen Gesellschaft fur Ernahrung, S. 117, no publication date available.
Arbeitsgemeinschaft fur Wirkstoffe in der Tierernahrung e.V.: Vitamine in der Tierernahrung, Bonn, 1991.
Recommended Dietary Allowance, 10$^{th}$ Ed., National Academy Press, 1998.

* cited by examiner

*Primary Examiner*—Raymond J. Henley, III
(74) *Attorney, Agent, or Firm*—Novak Druce & Quigg

(57) ABSTRACT

Compositions are proposed which comprise folic acid in combination with 5-methyltetrahydrofolic acid, and also compositions which comprise folic acid, 5-methyltetrahydrofolic acid and/or 5-methyltetrahydrofolylpolyglutamate and also comprise a dietary component and/or a nutrient preparation, and their use is also proposed.

14 Claims, No Drawings

COMPOSITIONS CONTAINING FOLIC ACID AND REDUCED FOLATE

This application is a national stage application filed under 35 U.S.C. §371 of international application PCT/EP 01/04984 filed May 3, 2001.

INTRODUCTION

The present invention relates to the field of human and animal nutrition and dietary supplementation and relates to compositions which comprise folic acid and 5-methyltetrahydrofolic acid and/or their polyglutamates. The invention also relates to the use of these compositions.

PRIOR ART

Folic acid (N-pteroyl-L-monoglutamic acid) is a widely occurring growth factor having the character of a vitamin. Folic acid itself does not occur in plant and animal foods.

The forms of folic acid which occur naturally are reduced folates in the form of polyglutamates. De-novo synthesis of these folates is only possible for microorganisms and plants. Before absorption, the polyglutamates are broken down to monoglutamates by the folate conjugase of the small intestine brush-border cells. Only the monoglutamates can be absorbed by the intestinal mucosa in an active transport process. The biologically inactive folic acid is reduced by the enzyme folate reductase to 7,8-dihydrofolic acid and by dihydrofolate reductase to 5,6,7,8-tetrahydrofolic acid (THF). THF is the actually physiologically active form of folic acid: THF is a transport metabolite for one-carbon species, their transfer proceeding via 5-methyltetrahydrofolate, 5,10-methylenetetrahydrofolate, 5-formyltetrahydrofolate (folic acid), 5-formiminotetrahydrofolate, 10-formyltetrahydrofolate or 5,10-methenyltetrahydrofolate. The C1 building blocks are required, inter alia, for the biosynthesis of purine nucleotides and of deoxythymidine-5'-monophosphate, that is to say as precursors of deoxyribonucleic acids (DNA).

Folate deficiency can occur due to deficient supply via the diet, increased requirement (for example during pregnancy and nursing, alcohol abuse), deficient absorption from the diet (for example as a consequence of celiac disease or sprue), due to simultaneous intake of antimetabolites (for example methotrexate or aminopterin, which are used in the course of chemotherapy as competitive inhibitors of difolate reductase, or sulfonamides which, as antimetabolites of 4-aminobenzoic acid, inhibit folate biosynthesis) or due to genetic dysfunction in one of the enzymes of folate metabolism, for example of methylenetetrahydrofolate reductase. The consequences of folate deficiency are disorders in amino acid metabolism and protein metabolism and in cell division (especially nucleic acid metabolism). This is expressed especially in rapidly proliferating tissues, for example bone marrow cells and can lead to megaloblastic anemia and thrombocytopenia and ultimately death. Folate deficiency is associated with disorders in growth and mental development of neonates. Epidemiological studies indicate that an increased incidence of neural tube defects (NTDs) in neonates, including spina bifida and anencephaly, which is correlated with a low folate status of the mothers. Supplementation of pregnant women with 0.4 to 4 mg of folic acid/day decreased the frequency of abnormalities in newborn infants by 50–80% (Hages et al., 1996, Geburtsh. Frauenheilk., 56, M59–M65).

The importance of folic acid in animal nutrition, especially in bearing progeny, is described for guinea pigs (Habibzadeh et al. 1986, Br. J. Nutr., Vol. 55, p. 23), also for breeding pigs (Friendship et al., 1991, In. Can. Vet. J., Vol 32, p. 564).

U.S. Pat. No. 4,753,926 describes foods for infants, in particular pre-term infants, which foods contain from 40 to 150 mg of folic acid/100 ml. Clinical studies verify the effectiveness of administering folic acid to pregnant women to prevent NTDs in newborn infants. The effect of folic acid on lowering the homocysteine level (risk factor for cardiovascular disorders) in the blood is also clinically verified (Hankey et al., 1999, Lancet, 354, 407–413). An intake of at least 400 mg of folic acid per day is necessary to have a beneficial effect on the blood homocysteine level. (Davis et al., 1994, Faseb J., 8, A248 abstract). The folates present in the diet (especially in leaf vegetables and cereals, and in liver) are sensitive to heat and light, so that even for healthy persons adequate supply via the diet cannot always be ensured. The cause of the low folate status in humans is considered to be chiefly due to the inadequate intake from the diet (Stampfer et al. 1995, N. Engl. J. Med., 322; 328–329).

For the reasons given above, an increase in folate supply via the diet by enriching food with folic acid, or the oral intake of folic acid, is recommended, for example, by the U.S. Food and Drug Administration (FDA). The German nutrition association Deutsche Gesellschaft für Ernährung (DGE) recommends a daily intake of 400 μg of folic acid/day for healthy adults. Correspondingly higher recommendations apply for pregnant women and nursing women (600 μg/day) (Referenzwerte für die Nährstoffzufuhr [Reference values for nutrient supply], $1^{st}$ edition, Umschau Braus Verlag, Frankfurt am Main, 2000, published by the DGE, p. 117). Folic acid in this case is the oxidized form of folates in the form of the monoglutamate (N-pteroyl-L-glutamic acid).

For animal nutrition, a folic acid supplementation of from 0.2 to 0.5 mg/kg of feed dry matter is recommended for poultry and pigs. However, under industrial animal production conditions, increasing the folic acid supplementation to 0.5–1.0 mg/kg of feed is recommended for poultry and 0.5–2.0 mg of feed for pigs (Arbeitsgemeinschaft für Wirkstoffe in der Tierernährung e.V.: Vitamine in der Tierernährung [Vitamins in animal nutrition], Bonn, 1991).

Since it has become known that an increased folic acid intake can mask a vitamin B12 deficiency and can thus lead to irreversible damage of the nervous system and to reoccurrence of epileptic attacks in epileptic patients that are being treated with antifolates, the permissible maximum amount of folic acid has been decreased, for example by the NRC (US Nutritional Research Council of the Academy of Sciences). A maximum of 3 mg/kg of body weight is now recommended for healthy adults, which corresponds to a daily intake of approximately 200 mg (Recommended Dietary Allowance, $10^{th}$ edition, National Academy Press, 1998) and, for pregnant or nursing women, permits daily intakes of 400 mg/day and 260–280 mg/day. However, these amounts cannot ensure adequate supply of the entire population (the desirable daily intake is estimated at 400 mg for healthy adults). In particular, groups of the population having a genetic defect in folate metabolism and/or absorption disorders cannot thus receive an adequate supply. A further restriction in folic acid supplementation is the unsatisfactory chemical stability of folic acid, depending on the formulation used. An adequate effective amount can only be ensured in products requiring relatively long term storage, as occurs especially in the case of animal nutrition, or with special foods, for example beverages, via an undesirable overdosing.

WO 97/27764 proposes the use of the naturally occurring isomers of reduced folates for enriching foods and dietary supplements. U.S. Pat. No. 5,624,686 proposes reduced folates for increasing the fat content of breeding pigs. The reduced folates are used as such or in the form of liver powder or microbial cell digests. EP 646 322 A1 describes an animal nutrition additive for pigs, which contains reduced folates in the form of 7,8-dihydrofolic acid, leucovorin (5-formyltetrahydrofolic acid) and/or microbial cell digests or cell extracts. WO 99/37155 proposes therapeutic compositions which contain at least 2 substances that are selected from the group consisting of tyrosine, methylating agents, phospholipids, fatty acids and St. John's Wort (*hypericum perforatum*). These preparations are proposed for the prevention and/or treatment of depressions and for the regulation of neurotransmitter levels.

However, in the case of these compositions it is not possible to exclude the fact that, in humans having a defect in folate conjugase, the breakdown of the reduced folic acid isomers from the polyglutamate to the monoglutamate cannot occur, and thus an intake of folates cannot be ensured. In addition, it is not possible to ensure that the administration of naturally occurring reduced folates can actually prevent, for example the formation of neural tube defects, or lowers the homocysteine level.

It is an object of the present invention to provide compositions which ensure an adequate folate supply in humans and animals. These compositions should ensure bioavailability of folates in all parts of the population and for animals. These compositions should be chemically stable and usable independently of the formulation in foods, animal nutrition and food supplements for humans and animals. It was of particular interest to provide preparations which guarantee adequate folate supply for humans and animals having the most varied disorders in folate metabolism (including genetic defects or absorption disorders). In addition it would be desirable to obtain compositions which, with respect to their activity (increasing folate status in blood, prevention of folate deficiency symptoms etc.) have a synergistic effect compared with the prior art compositions.

We have found that this object is achieved, surprisingly, by the inventive preparations. It is thus possible to ensure the folate supply for humans and animals (via the addition of folic acid) and simultaneously to provide the amounts of folates required in order to achieve the preventive effects but which cannot be achieved by adding folic acid in a form which is harmless to health (by adding 5-methyltetrahydrofolic acid and/or its polyglutamates).

Surprisingly, we have found that by means of the inventive preparations, a synergistic increase in the folate status in blood plasma can be achieved. In addition, we have found that the naturally occurring reduced folates increase the stability of folic acid in an unexpected manner. This enables an addition to a multiplicity of foods and substances for dietary supplementation and thus guarantees stable contents even in the event of relatively long term storage. Surprisingly, we have found that the preparations are suitable for reliable (and substantially independent of defects in folate metabolism) folate supply in animals and humans having very varied folate metabolism defects. In particular, it is possible to supply the doses necessary to prevent neural defects and to prevent cardiovascular disorders and simultaneously to exclude a health risk (masking pernicious anemia, irreversible neuropathy).

DESCRIPTION OF THE INVENTION

The invention relates to compositions comprising
(a) folic acid
(b) 5-methyltetrahydrofolic acid and/or 5-methyltetrahydrofolylpolyglutamate
(c) a dietary component and/or a nutrient preparation
in which, if (c) is a dietary component, the amount of (b) in the composition (=Z) is greater than the amount of (b) in the dietary component (=N).

The invention further relates to compositions comprising
(a) folic acid
(b) 5-methyltetrahydrofolic acid.

Folic Acid (N-[4-(2-Amino-3,4-dihydro-4-oxo-6-pteridinylmethylamino)-benzoyl]-L-glutamic acid; also N-pteroyl-L-glutamic acid) can be synthesized via a number of routes. A review of these is given in Ullmanns Encyclopedia of Industrial Chemistry, VCH-Weinheim, Updated Sixth Edition, 1999 Electronic Release, Chapter 13.6. Folic acid can be present as free acid and in the form of physiologically acceptable salts, in particular as alkali metal salt and/or alkaline earth metal salt and as ammonium salt. Those which may be mentioned are, for example, the sodium salt, potassium salt, magnesium salt or calcium salt of folic acid. Particular preference is given to free folic acid.

5-Methyltetrahydrofolic acid and the polyglutamates

The term 5-methyltetrahydrofolic acid (5-MTHF) is taken to mean the compound N-(5-methyl)-5,6,7,8-tetrahydropteroyl)-L-glutamic acid both as a racemate (diastereoisomeric pair (6R,S) and (6S,S)) and in the form of the individual isomers (termed (6R) and (6S) isomers below). 5-MTHF is the monoglutamate. The polyglutamates are derived from 5-MTHF; in the polyglutamates from 2 to 8 glutamic acid radicals are linked in the γ position to the glutamic acid of 5-MTHF. The polyglutamates can also be present as diastereoisomers and in the form of the individual isomers.

5-Methyltetrahydrofolic acid can be synthesized from folic acid by methylation and hydrogenation (for example as described in DE 2807393 C2). Since folic acid contains the (S) configuration of glutamic acid, the two tetrahydrofolic acid diastereomers which form have the (6S,S) or (6R,S) configuration. The diastereomers can be separated, for example, by fractional crystallization (EP 0 455 013 A1) or using N-ethyl-2-aminomethylpyrrolidine (EP 0 612 322 B1). Processes are also known for the enantioselective synthesis of (6R) or (6S) 5-methyltetrahydrofolic acid (U.S. Pat. No. 5,350,8519 [sic]) and for the diastereoselective hydrogenation of folic acid in the presence of a chiral, immobilized rhodium(I)/diphosphine catalyst (EP 0 551 624 A1). 5-Methyltetrahydrofolylpolyglutamates can be obtained by isolation from natural sources, for example spinach, broccoli or pigs liver. 5-Methyltetrahydrofolic acid and the polyglutamates can be present as free acid or in the form of physiologically acceptable salts, in particular as alkali metal salt and/or alkaline earth metal salt and as ammonium salt. Those which may be mentioned in particular in this case are the sodium salt, potassium salt, magnesium salt or calcium salt. In a preferred embodiment of the present invention, 5-methyltetrahydrofolic acid is used, in particular the potassium salt of 5-methyltetrahydrofolic acid pentahydrate. 5-Methyltetrahydrofolic acid and the polyglutamates can be used as racemate (diastereomers (6R,S) and (6S,S)) and/or in the form of the individual isomers [(6S), (6R)]. In a preferred embodiment, 5-methyltetrahydrofolic acid and the polyglutamates are used predominantly (>50, in particular >75,% by weight, particularly preferably >80% by weight) in the form of the (6S) isomer, in particular exclusively as (6S) isomer. Particular preference is given to use of the (6S) isomer of 5-methyltetrahydrofolic acid.

The amount of 5-methyltetrahydrofolic acid and/or 5-methyltetrahydrofolylpolyglutamate can be chosen freely by those skilled in the art depending on the requirements of humans and animals. When 5-methyltetrahydrofolylpolyglutamates are used, there is an appropriate conversion calculation to 5-methyltetrahydrofolic acid (monoglutamate).

For the purposes of the present invention, folates means folic acid, 5-methyltetrahydrofolic acid and other reduced folates (monoglutamates and polyglutamates). In a preferred embodiment, the compositions comprise at least one other reduced folate. Other reduced folates are 7,8-dihydrofolate; 5,6,7,8-tetrahydrofolate; 5,10-methylenetetrahydrofolate; 5-formyltetrahydrofolate; 5-formiminotetrahydrofolate; 10-formyltetrahydrofolate and 5,10-methenyltetrahydrofolate. The reduced folates can be present as monoglutamates and as polyglutamates (from 2 to 8 glutamic acid residues). The reduced folates could be used as racemate (diastereomers (6R,S) and (6S,S)) and/or in the form of the individual isomers [(6S), (6R)]. In a preferred embodiment of the present invention, the reduced folates are used predominantly (>50, in particular >75, % by weight, particularly preferably >80% by weight), in particular exclusively, as (6S)-isomer.

Dietary Component

Dietary components are all substances which comprise one or more amino acids, carbohydrates or fat which are suitable for human and/or animal nutrition and are not nutrient preparations. The dietary component can be composed of one or more individual components. The individual components are components which essentially originate from a natural source. Typical individual components are sugar, fruit juice, nectar, fruit pulp or puree from a plant, for example apple juice, grapefruit juice, orange juice, apple puree, tomato sauce, tomato juice, tomato puree. Other typical individual components are cereal products from a cereal species, for example wheat flour, rye flour, oatmeal, corn flour, barley and dinkel flour, corn syrup and starches of said cereals. Typical individual components are, in addition, milk products such as milk protein, whey, yoghurt, lecithin and lactose.

In a preferred embodiment of the present invention, the dietary component is composed of 2 or more individual components. Typical examples of dietary components which are composed of 2 or more individual components are infant food, breakfast preparations, especially in the form of mueslis or bars, sports drinks, complete meals, especially in the context of completely balanced diets, dietetic preparations, such as diet drinks, diet meals and diet bars. The dietary component in these cases (or one of its individual components) can already contain folates or be free of folates. If the dietary component already comprises component (b) [5-methyltetrahydrofolic acid and/or 5-methyltetrahydrofolylpolyglutamate(s)], the amount of (b) in the composition (Z) is greater than the amount of (b) in the dietary component (N). The ratio Z/N is generally >1.05, in particular >1.2, particularly preferably >2.0.

Nutrient Preparation

Nutrient preparations consist of one or more essential nutrients. Essential nutrients in this case are all substances which are essential to life for humans and animals but which they cannot synthesize themselves (or not in a sufficient amount). These include in particular vitamins, provitamins, trace elements, amino acids and fatty acids. The essential amino acids are isoleucine, leucine, lysine, methionine, phenylalanine, threonine, tryptophan and valine. Semi-essential amino acids are also included, which must be supplied, for example, in growth phases or deficiency states, such as arginine, histidine, cysteine and tyrosine. Trace elements are: essential trace elements whose necessity has been proved for humans and whose deficiency leads to the manifestation of clinical symptoms: iron, copper, zinc, chromium, selenium, calcium, magnesium, potassium, lithium, cobalt, molybdenum, iodine, silicon, fluorine, manganese. In addition elements whose function for humans has not yet been adequately confirmed: tin, nickel, vanadium, arsenic, manganese. Fatty acids which are essential for humans are: linoleic acid and linolenic acid. A comprehensive listing of vitamins may be found in Referenzwerte für die Nährstoffzufuhr [Reference values for nutrient supply], 1$^{st}$ edition, Umschau Braus Verlag, Frankfurt am Main, 2000, published by the DGE. Typical nutrient preparations are vitamin preparations, multivitamin preparations, mineral preparations, multimineral preparations and dietary supplements.

For the purposes of the present invention, nutrient preparations are, especially, those which comprise at least one nutrient of at least 15, preferably 25, in particular 50%, of the daily requirement.

The nutrient preparations may be produced, using the conventional aids (fillers, emulsifiers, tableting aids etc.) by known methods, for example in the form of tablets, capsules or powders. Examples of aids are soluble or insoluble polyvinylpyrrolidones and vinylpyrrolidone/vinylacetate copolymers, as are obtainable, for example, under the trade name Kollidon®. In addition, tableting aids based on lactose monohydrate may be mentioned and granules from lactose monohydrate and soluble or insoluble polyvinylpyrrolidones, as are obtainable, for example, under the trade name Ludipress®. These preparations can also comprise colors and flavors.

In a preferred embodiment, the compositions comprise as further constituent vitamins, in particular vitamin B6 and/or vitamin B12. Generally, the compositions comprise the vitamins in amounts from 50 to 200% of the daily requirement, in particular in amounts from 75 to 150% of the daily requirement, in particular 100%.

In a further embodiment of the invention, the compositions can comprise as further constituent S-adenosylmethionine. S-Adenosylmethionine [S-(5'-deoxyadenosyl)-L-methionine] is the most important methyl group donor in cellular metabolism. These compositions usually comprise from 20 to 800 mg, in particular from 50 to 200 mg, of S-adenosylmethionine. Surprisingly, it has been found that these compositions are particularly suitable for the prevention and/or treatment of cardiovascular disorders.

The inventive compositions customarily comprise
(a) from 0.2 to 15 mg, in particular from 0.4 to 5, preferably from 2 to 4 mg of folic acid
(b) from 0.4 to 40 mg, in particular from 0.8 to 10, preferably from 4 to 8 mg, of 5-methyltetrahydrofolic acid and/or 5-methyltetrahydrofolylpolyglutamate, particularly preferably (6S)-5-methyltetrahydrofolic acid.

They can further comprise
(c) from 5 to 50 mg, in particular 10 mg, of vitamin B6
(d) from 0.2 to 1 mg, in particular 0.4 mg, of vitamin B12
(e) from 20 to 800 mg, in particular 50 to 400, preferably from 100 to 250 mg, of S-adenosylmethionine.

The inventive compositions are suitable for the nutrition and/or dietary supplementation of humans and animals. In particular, they are suitable for the nutrition and/or dietary supplementation of humans having an increased folate requirement. The present invention therefore further relates to the use of the compositions as claimed in claim 1 and/or 2 for the nutrition and/or dietary supplementation of humans and/or animals.

In a preferred embodiment of the present invention, the preparations which are suitable for human nutrition comprise from 5 to 200%, preferably from 10 to 200, in particular from 50 to 100%, of the daily requirement (as recommended by the DGE) of folates in the form of folic acid. Preferably, the use of folic acid is less than or equal to 100%, in particular less than or equal to 50%, of the daily requirement. The amount of folates is expressed in % of daily requirement and thus incorporates changes in knowledge of human requirements and the differing requirements according to life status (age, sex, health status, weight). The daily amount of folic acid recommended by the DGE is currently 60 µg for 0–4 month-old suckling infants, 80 µg for 4–12 month-old suckling infants, 200 µg for 1–4-year-old infants, 300 µg for 4–10-year-old children, 400 µg for children from 10 years old and healthy adults and 600 µg for pregnant and nursing women. (Referenzwerte für die N ährstoffzufuhr [Reference values for the supply of nutrients], 1$^{st}$ edition, Umschlau Braus Verlag, Frankfurt am Main, 2000, published by the DGE, p. 117). Therefore, the preparations for children from 10 years old and healthy adults in their preferred embodiment comprise from 20 to 800 µg, preferably from 40 to 800 µg, of folic acid, in particular from 200 to 400 µg of folic acid. Correspondingly, the preparations for infants from 1 to 4 years old comprise in their preferred embodiment from 10 to 400 µg, in particular from 20 to 400 µg, particularly preferably from 100 to 200 µg of folic acid. In a particularly preferred embodiment of the present invention, the preparations for human nutrition comprise a maximum of 100% of the daily requirement (for example for children from 10 years old and healthy adults currently 400 µg of folic acid), in particular a maximum of 50% of the daily requirement (for example for children from 10 years old and healthy adults currently a maximum of 200 µg of folic acid).

In a preferred embodiment of the present invention, the preparations which are suitable for animal nutrition comprise from 5 to 3000%, preferably from 10 to 2000, in particular from 50 to 1000%, of the daily requirement of folates in the form of folic acid. The amount of folates is expressed in % of daily requirement and thus incorporates changes in the knowledge of the animal requirement. The daily requirement for various animals is customarily reported in mg of folic/kg of animal feed and varies depending on the animal species. Usually the amounts are from 0.1 to 5.0, in particular from 0.2 to 3.0, preferably from 0.5 to 1.5, mg of folic acid/kg of animal feed. In a particularly preferred embodiment of the present invention, the preparations for animal nutrition comprise a maximum of 5 mg of folic acid/kg of animal feed.

This daily dose can be achieved in the form of a single dose or in the form of a plurality of partial doses. The preparations can be used over days, weeks, months or years.

Compositions which are particularly suitable for human nutrition and/or dietary supplementation are those which comprise
(a) 400, in particular 200, µg of folic acid
(b) 800, in particular 400, µg of 5-methyltetrahydrofolic acid and/or 5-methyltetrahydrofolylpolyglutamate, preferably (6S)-5-methyltetrahydrofolic acid.

The folate status of humans and animals can be determined using methods known to those skilled in the art, for example via the serum folate concentration or via the erythrocyte folate concentration. It is also known to measure the plasmahomocysteine level as a functional indicator for folate status.

The inventive compositions are also suitable for women of child-bearing age and pregnant women for preventing neural tube defects in fetuses and/or neonates. The invention therefore further relates to the use of the compositions as claimed in claim 1 and/or 2 for producing drugs for women of child-bearing age and/or pregnant women for preventing neural tube defects in fetuses and/or neonates. It has proved advantageous to use for this compositions which comprise
(a) 400, in particular 200, µg of folic acid
(b) 800, in particular 400, µg of 5-methyltetrahydrofolic acid and/or 5-methyltetrahydrofolylpolyglutamate, preferably (6S)-5-methyltetrahydrofolic acid.

In a preferred embodiment of the present invention, preparations which comprise
(a) from 1 to 4, in particular 2, mg of folic acid
(b) from 1 to 8, in particular 4, mg of 5-methyltetrahydrofolic acid and/or 5-methyltetrahydrofolylpolyglutamate, preferably (6S)-5-methyltetrahydrofolic acid are used to produce drugs for women of child-bearing age and/or pregnant women for preventing neural tube defects in fetuses and/or neonates, if these women have already borne a child having a neural tube defect or have had a miscarriage owing to a neural tube defect.

In a particularly preferred embodiment these preparations comprise 2 mg of folic acid and 4 mg of 5-methyltetrahydrofolic acid, in particular 2 mg of folic acid and 4 mg of (6S)-5-methyltetrahydrofolic acid.

The inventive compositions are further suitable for the prevention and/or treatment of cardiovascular disorders. The invention therefore further relates to the use of the compositions as claimed in claim 1 and/or 2 for producing drugs for the prevention and/or treatment of cardiovascular disorders. It has proved advantageous to use for this compositions which comprise
(a) from 1 to 15, in particular from 2 to 4, mg of folic acid
(b) from 1 to 40, in particular from 4 to 10, mg of 5-methyltetrahydrofolic acid and/or 5-methyltetrahydrofolylpolyglutamate, preferably (6S)-5-methyltetrahydrofolic acid.

Surprisingly, it has been found that these compositions are suitable in particular for the prevention of cardiovascular disorders in patients having chronic kidney failure.

EXAMPLES

Example 1

Enriching Flour with 10 ppm of MTHF (as Calcium Salt) and 5 ppm of Folic Acid:

13.75 mg of MTHF calcium salt (corresponding to 10 mg of active compound) and 5.5 mg of folic acid (water content 8%) are triturated to homogeneity in a mortar together with 2 g of wheat flour type 405. A further 18 g of wheat flour are added to this trituration and mixing is repeated. The mixture is then incorporated into 200 g of wheat flour using a Stephan mixer (type UMC 5 electronic). After addition of a further 780 g of wheat flour, mixing is carried out at 800 rpm for approximately 20 minutes.

100 g of this flour comprise 1000 µg of 5-methyltetrahydrofolic acid and 500 µg of folic acid

Example 2

| Soft drink containing 4 ppm of MTHF (as calcium salt) and 2 ppm of folic acid: | |
|---|---|
| Sugar (sucrose) | 10.50% |
| Citric acid | 0.75% |
| Orange flavor (Firmenich product No. 503.986) | 0.15% |
| Ascorbic acid | 0.04% |
| β-Carotene (as Lucarotin 10 CWD) | 5 ppm |
| MTHF—Ca (calcium salt pentahydrate) | 5.5 ppm (equivalent to 4 ppm of active compound) |
| Folic acid (water content 8%) | 2.2 ppm |
| Water | to 100% |

All figures in % by weight.

Sugar, citric acid, ascorbic acid and orange flavor are stirred into 10 kg of water and dissolved or homogeneously mixed. β-Carotene powder, MTHF-Ca and folic acid are dissolved or dispersed in 200 ml of water and added to the above mixture. The mixture is then made up to 20 kg with water. The batch is heated to 90° C. for 30 seconds in a short-time heating system and then packaged in 200 ml glass bottles.

100 g of this soft drink comprise 400 µg of 5-methyltetrahydrofolic acid and 200 µg of folic acid.

Example 3

Tablets Containing 400 µg of MTHF (as Ca Salt) and 200 µg of Folic Acid.

| Formulation (weights per tablet): | |
|---|---|
| MTHF—Ca | 550 µg mg [sic] (≈ 400 µg of MTHF) |
| Folic acid | 220 µg (≈ 200 µg of folic acid) |
| Kollidon ® CLM [1] | 5 mg |
| Ludipress ® LCE [2] | 93.23 mg |
| Mg stearate | 1 mg |
| Tablet weight | 100 mg. |

All of the ingredients are mixed in a tumble mixer (Tubula) for 10 minutes and then passed twice through a sieve having a mesh width of 800 µm. The mixture is pressed on a Korsch PH 106 tablet press at a pressing force of approximately 25 kN to form tablets having a diameter of 6 mm.

Example 4

Tablets Containing 400 µg of 6S-isomer of MTHF (as Ca Salt) and 200 µg of Folic Acid

| Formulation (weight per tablet): | |
|---|---|
| (6S) isomer MTHF—Ca | 550 µg mg [sic] (≈ 400 µg of MTHF) |
| folic acid | 220 µg (≈ 200 µg of folic acid) |
| Kollidon ® CLM [1] | 5 mg |
| Ludipress ® LCE [2] | 93.23 mg |
| Mg stearate | 1 mg |
| Tablet weight: | 100 mg. |

All of the ingredients are mixed in a tumble mixer (Tubula) for 10 minutes and then passed twice through a sieve having a mesh width of 800 µm. The mixture is pressed on a Korsch PH 106 tablet press at a pressing force of approximately 25 kN to form tablets having a diameter of 6 mm.

1) Polyvinylprrrolidone-based aid
2) direct tableting aid based on lactose monohydrate and polyvinylpyrrolidone

Example 5a

Multivitamin/Multimineral Tablet Containing 400 μg of MTHF and 200 μg of Folic Acid

| Formulation (weight/100 g) | | | |
|---|---|---|---|
| Calcium hydrogen phosphate | 52.1 g | ManganeseII sulfate | 231 mg |
| Magnesium oxide | 12.42 g | Vitamin B6 | 150 mg |
| Potassium chloride | 5.71 g | Vitamin B2 | 120 mg |
| Vitamin C | 4.49 g | Vitamin B1 | 105 mg |
| Nicotinamide | 1.35 g | Copper oxide | 93.71 mg |
| Vitamin E | 749 mg | β-Carotene | 89.89 mg |
| Zinc oxide | 466 mg | Vitamin A | 44.94 mg |
| Calcium D-pantothenate | 449 mg | Potassium iodide | 29.36 mg |
| Biotin | 11.24 mg | ChromiumIII chloride | 10.56 mg |
| IronII fumarate | 912 mg | Sodium molybdate | 5.17 mg |
| Sodium selenate | 4.94 mg | Vitamin K1 | 2.25 mg |
| Sodium metasilicate | 1.65 mg | Vitamin B 12 | 0.07 mg |
| Vitamin D3 | 0.37 mg | | |
| Folic acid | 14,98 mg | | |
| MTHF Ca salt | 33.3 mg | | |

Stearic acid, magnesium stearate, silicon dioxide, emulsifier E433, fillers E460, E464, polyvinylpyrrolidone This mixture is pressed into tablets of 1.335 g. Per tablet it contains 400 μg of folic acid and 400 μg of MTHF.

Example 5b

Multivitamin/Multimineral Tablet Containing 400 μg of (6S)MTHF and 200 μg of Folic Acid A mixture as in Example 5a was produced, but instead of 5-MTHF Ca salt, 33.3 mg of (6S)-MTHF were added.

Example 6

Breakfast Preparation (Muesli)

Cereal flakes, sugar, salt and malt syrup are mixed, so that one portion (30 g) comprises 2 g of protein and 26 g of carbohydrates. To this mixture are added Vitamin A 750 I.U.; vitamin C 15 mg; vitamin D: 40 I.U., vitamin B1 (thiamin) 1.5 mg; vitamin B2 (riboflavin) 1.7 mg; niacin 5 mg; vitamin B6 0.5 mg; folic acid 220 μg (equivalent to 200 μg), MTHF Ca salt 440 μg (equivalent to 400 μg of MTHF).

Example 7

Breakfast Preparation (Muesli)

A mixture as in Example 6 was produced, but instead of 5-MTHF Ca salt, 440 μg of (6S)-MTHF were added.

Example 8

Preparation for Pregnant Women Who Have Already Borne a Child with NTD

| | |
|---|---|
| (6S)-Isomer MTHF Ca | 5.5 mg (≈ 4.0 mg of MTHF) |
| Folic acid | 2.2 mg (≈ 2.0 mg of folic acid) |
| Kollidon ® CLM [1)] | 5 mg |
| Ludipress ® LCE [2)] | 86.3 mg |
| Mg stearate | 1 mg |
| Tablet weight: | 100 mg |

Example 9

Preparation for the Prevention of Cardiovascular Disorders

| | |
|---|---|
| (6S)-Isomer MTHF Ca | 13.75 mg (≈ 10.0 mg of MTHF) |
| Folic acid | 5.5 mg (≈ 5.0 mg of folic acid) |
| Kollidon ® CLM [1)] | 5 mg |
| Ludipress ® LCE [2)] | 74.75 mg |
| Mg stearate | 1 mg |
| Tablet weight: | 100 mg |

We claim:

1. A composition comprising
   (a) folic acid,
   (b) 5-methyltetrahydrofolic acid and/or 5-methyltetrahydrofolyl-polyglutamate,
   (c) a dietary component and/or a nutrient preparation,
   (d) vitamin B6 and/or vitamin B12, and
   (e) S-adenosylmethionine,
   wherein, if (c) is a dietary component, the amount of (b) in the composition is greater than the amount of (b) in the dietary component (c).

2. The composition defined in claim 1, wherein component (b) is 5-methyl-(6S)-tetrahydrofolic acid and/or 5-methyl-(6S)-tetrahydrofolylpolyglutamate.

3. The composition defined in claim 1, which further comprises at least one compound which is selected from the group consisting of tetrahydrofolic acid, dihydrofolic acid, 5-formyltetrahydrofolic acid, 10-formyltetrahydrofolic acid, 5,10-methylenetetrahydrofolic acid, 5,10-methenyltetrahydrofolic acid, 5-formiminotetrahydrofolic acid and their polyglutamate derivatives.

4. The composition defined in claim 1, which further comprises one or more vitamins as additional constituents.

5. A method of preventing or treating a folate deficiency in a human or animal, which comprises administering to said human or animal an effective amount of the composition defined in claim 1.

6. The method of claim 5, wherein the composition is administered to said human in an amount which provides for from 5 to 200% of said human's daily folic acid requirement.

7. The method of claim 5, wherein said human is a woman capable of childbearing, a pregnant woman or a newborn infant.

8. The method of claim 5, wherein the composition is administered to said animal in an amount which provides for from 5 to 3000% of said animal's daily folic acid requirement.

9. A method of preventing neural tube defects in a newborn infant, which comprises administering to the mother of said infant during her pregnancy with said infant an effective amount of the composition defined in claim 1.

10. A composition comprising (a) folic acid,
(b) 5-methyl-(6S)-tetrahydrofolic acid and/or 5-methyl-(6S)-tetrahydrofolylpolygutamate, and
(c) S-adenosylmethionine.

11. A composition as claimed in claim 10, which further comprises vitamin B6 and/or vitamin B12.

12. A composition as claimed in claim 10, which further comprises at least one compound which is selected from the group consisting of tetrahydrofolic acid, dihydrofolic acid, 5-formyltetrahydrofolic acid, 10-formyltetrahydrofolic acid, 5,10-methylenetetrahydrofolic acid, 5,10-methenyltetrahydrofolic acid, 5-formiminotetrahydrofolic acid and their polyglutamate derivatives.

13. A method of preventing or treating a folate deficiency in a human or animal, which comprises administering to said human or animal an effective amount of the composition defined in claim 10.

14. A method of preventing neural tube defects in a newborn infant, which comprises administering to the mother of said infant during her pregnancy with said infant an effective amount of the composition defined in claim 10.

* * * * *

UNITED STATES PATENT AND TRADEMARK OFFICE
CERTIFICATE OF CORRECTION

PATENT NO. : 6,921,754 B1 Page 1 of 1
APPLICATION NO. : 10/275566
DATED : July 26, 2005
INVENTOR(S) : Hähnlein et al.

It is certified that error appears in the above-identified patent and that said Letters Patent is hereby corrected as shown below:

On the cover page, please delete the PCT publication date and replace it with the following:
PCT Pub. Date: Nov. 15, 2001

In Claim 1, column 12, line 25 please delete:
"5-methyltetrahydrofolyl-polyglutamate" and substitute therefore:

-- 5-methyltetrahydrofolylpolyglutamate --.

Signed and Sealed this

Nineteenth Day of December, 2006

JON W. DUDAS
*Director of the United States Patent and Trademark Office*